(12) United States Patent
Kemp, II et al.

(10) Patent No.: US 9,805,417 B2
(45) Date of Patent: Oct. 31, 2017

(54) SYSTEM AND METHOD FOR AUTOMATED TRADING

(75) Inventors: Gary Allan Kemp, II, Winnetka, IL (US); Joan Ebersole, Glen Ellyn, IL (US); Robert J. Kline, Chicago, IL (US)

(73) Assignee: Trading Technologies International, Inc., Chicago, IL (US)

( * ) Notice: Subject to any disclaimer, the term of this patent is extended or adjusted under 35 U.S.C. 154(b) by 1768 days.

(21) Appl. No.: 10/284,584

(22) Filed: Oct. 31, 2002

(65) Prior Publication Data

US 2003/0236737 A1 Dec. 25, 2003

Related U.S. Application Data

(60) Provisional application No. 60/389,794, filed on Jun. 19, 2002.

(51) Int. Cl.
*G06Q 40/04* (2012.01)
*G06Q 40/06* (2012.01)

(52) U.S. Cl.
CPC .................... *G06Q 40/04* (2013.01)

(58) Field of Classification Search
CPC ......... G06Q 40/04; G06Q 40/06; G06Q 40/00
USPC ..................................... 705/35–37
See application file for complete search history.

(56) References Cited

U.S. PATENT DOCUMENTS

| | | |
|---|---|---|
| 4,674,044 A | 6/1987 | Kalmus |
| 5,101,353 A | 3/1992 | Lupien |
| 5,787,402 A | 7/1998 | Potter et al. |
| 5,799,287 A | 8/1998 | Dembo |
| 5,819,238 A | 10/1998 | Fernholz |
| 6,014,643 A | 1/2000 | Minton |
| 6,134,535 A | 10/2000 | Belzberg |
| 6,282,521 B1 | 8/2001 | Howorka |

(Continued)

FOREIGN PATENT DOCUMENTS

| | | |
|---|---|---|
| EP | 1067471 A1 | 1/2001 |
| EP | 1104904 A1 | 6/2001 |

(Continued)

OTHER PUBLICATIONS

International Search Report for PCT/US03/19328.

(Continued)

*Primary Examiner* — Hao Fu
(74) *Attorney, Agent, or Firm* — McDonnell Boehnen Hulbert & Berghoff LLP

(57) ABSTRACT

An automated trader facilitates automatic trading of tradeable objects over one or more electronic exchanges. According to one embodiment, an automated trader utilizes a user programmable interface. The user programmable interface allows the user to simply develop a program that is based on a set of specifications and relationships given by the user and input into a profile, or if desired, input directly into the programmable interface referred to as direct entry. For each tradeable object, a profile may be selected, and then an automated trader can execute the program to perform a series of actions according to that selected profile and directed order entry, if any. An automated trader may also be used at a communication level to create an intelligent interface between third-party trading-related applications and exchanges.

36 Claims, 10 Drawing Sheets

(56) References Cited

U.S. PATENT DOCUMENTS

| | | | |
|---|---|---|---|
| 6,408,282 B1 * | 6/2002 | Buist | 705/36 R |
| 6,418,419 B1 | 7/2002 | Nieboer | |
| 6,772,132 B1 | 8/2004 | Kemp, II | |
| 6,938,011 B1 | 8/2005 | Kemp, II | |
| 6,996,540 B1 * | 2/2006 | May | 705/37 |
| 7,246,092 B1 * | 7/2007 | Peterson et al. | 705/37 |
| 7,356,499 B1 | 4/2008 | Amburn | |
| 2002/0046146 A1 | 4/2002 | Otero | |
| 2002/0046149 A1 | 4/2002 | Otero | |
| 2002/0046151 A1 * | 4/2002 | Otero et al. | 705/37 |
| 2002/0046156 A1 | 4/2002 | Horn | |
| 2002/0049661 A1 | 4/2002 | Otero | |
| 2002/0128950 A1 | 9/2002 | Wu | |
| 2002/0138400 A1 * | 9/2002 | Kitchen et al. | 705/37 |
| 2002/0138401 A1 | 9/2002 | Allen | |
| 2002/0174058 A1 * | 11/2002 | Baghdady | 705/37 |
| 2003/0033235 A1 | 2/2003 | Hummelgren | |
| 2003/0093352 A1 | 5/2003 | Muralidhar et al. | |
| 2003/0200167 A1 | 10/2003 | Kemp | |
| 2004/0210511 A1 * | 10/2004 | Waelbroeck et al. | 705/37 |
| 2007/0100735 A1 | 5/2007 | Kemp | |

FOREIGN PATENT DOCUMENTS

| | | |
|---|---|---|
| EP | 1217564 A2 | 6/2002 |
| EP | 1217564 A3 | 7/2002 |
| EP | 1246111 A2 | 10/2002 |
| WO | WO9114231 A1 | 9/1991 |
| WO | WO95/26005 A1 | 9/1995 |
| WO | WO9849639 A1 | 11/1998 |
| WO | WO9919821 A1 | 4/1999 |
| WO | WO99/30259 A1 | 6/1999 |
| WO | WO00/48113 A1 | 8/2000 |
| WO | WO00/51043 A1 | 8/2000 |
| WO | WO00/52619 A1 | 9/2000 |
| WO | WO00/62187 A2 | 10/2000 |
| WO | WO0062187 A3 | 10/2000 |
| WO | WO00/65510 A1 | 11/2000 |
| WO | WO01/16830 A1 | 3/2001 |
| WO | WO01/16852 A2 | 3/2001 |
| WO | WO01/16852 C1 | 3/2001 |
| WO | WO01/22266 A2 | 3/2001 |
| WO | WO01/22315 A2 | 3/2001 |
| WO | WO0122315 A3 | 3/2001 |
| WO | WO01/88808 A1 | 11/2001 |
| WO | WO02/33621 A1 | 4/2002 |
| WO | WO02/33623 A1 | 4/2002 |
| WO | WO02/33635 A1 | 4/2002 |
| WO | WO02/33636 A1 | 4/2002 |
| WO | WO02/33637 A1 | 4/2002 |
| WO | WO02/47006 A1 | 6/2002 |
| WO | WO02080433 | 10/2002 |
| WO | WO03077061 A2 | 9/2003 |
| WO | WO03077061 A3 | 9/2003 |

OTHER PUBLICATIONS

USPTO Presentation, NASDAQ, Nov. 8, 2001.
Kharouf, A Trading Room with a View, Futures, 27, 11—Nov. 1998.
www.tradingtechnologies.com/products/xtrade_full.html (viewed May 22, 2001) Jun. 9, 2000.

* cited by examiner

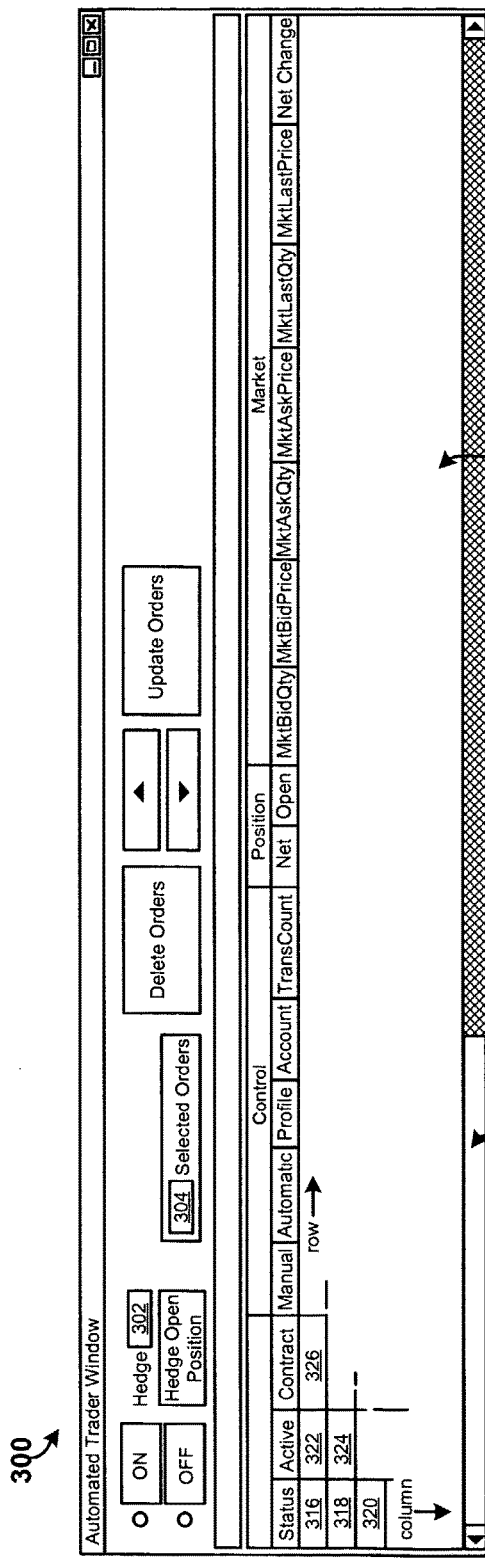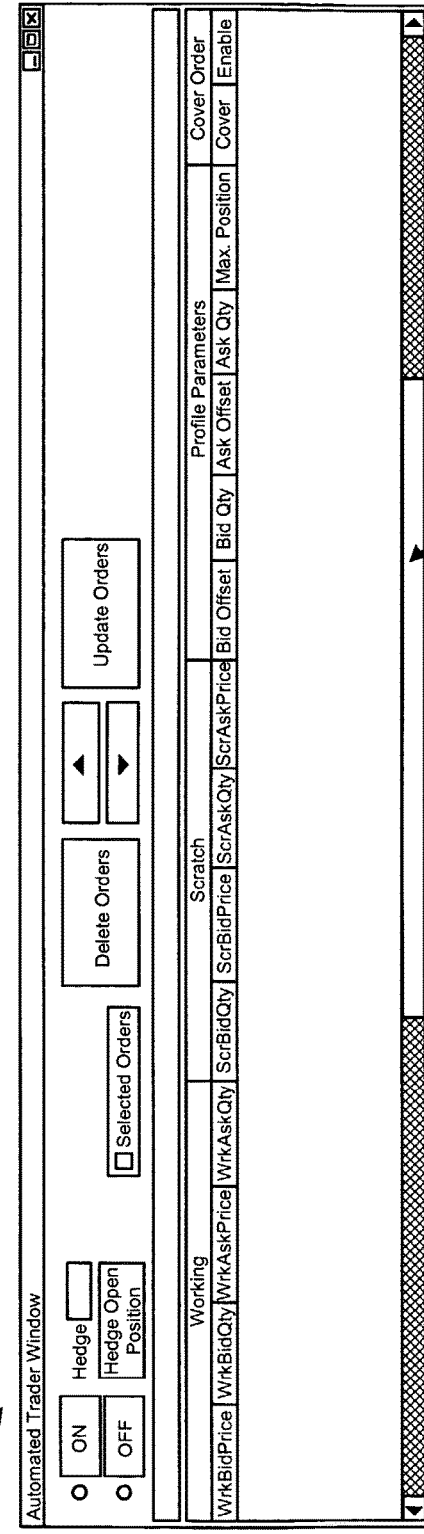
FIG. 4
FIG. 5

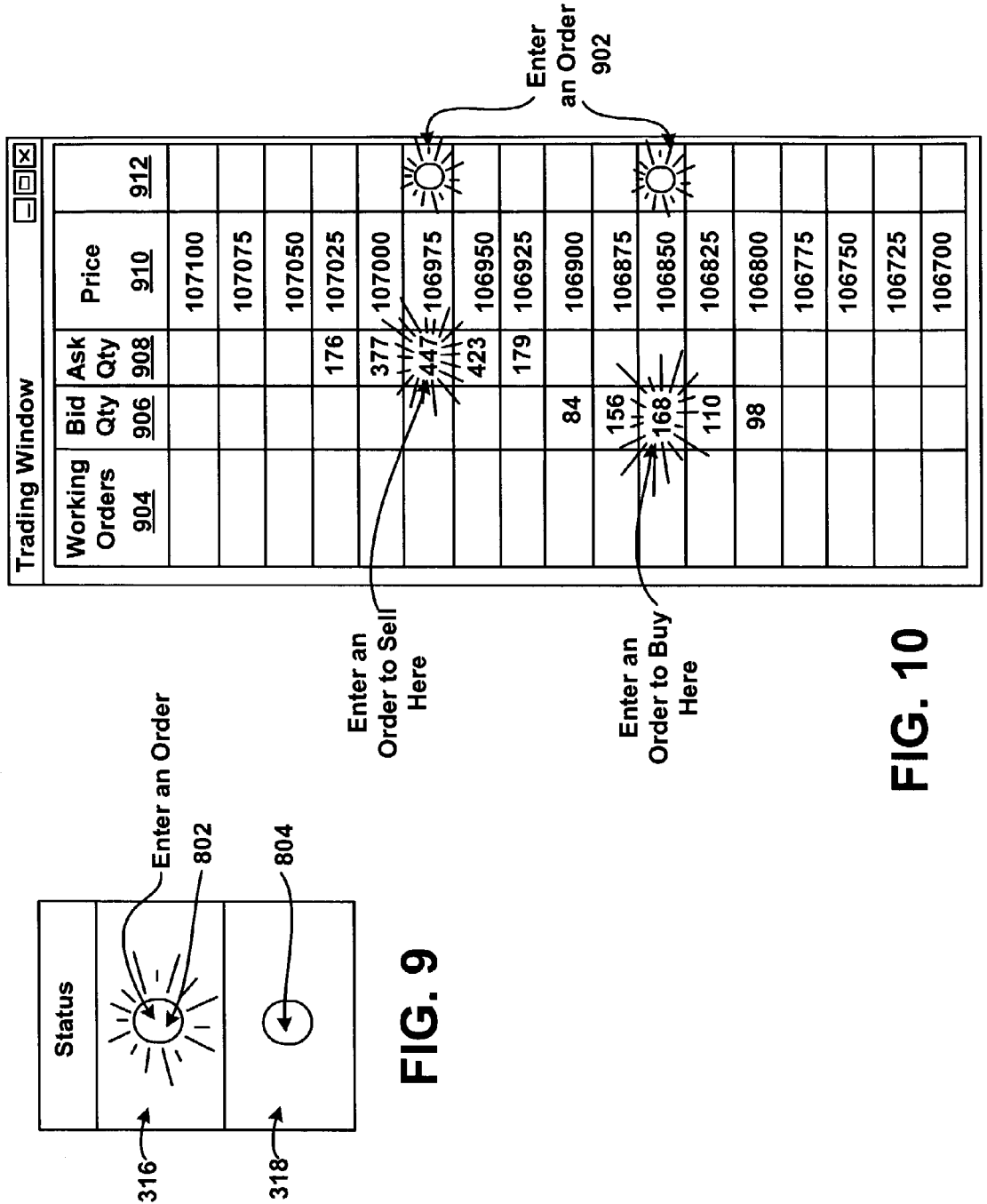

Profiles

| | |
|---|---|
| 812 | |

Name 810

| New 804 | Save 806 | Delete 802 |

| Account | ABC ▶ |
|---|---|
| Profile Base Price | Market ▶ |
| Throttle Quoting | ☐ 500 Millisecs between Quotes |
| Enable Cover Orders | ☐ Cover Order Color |
| Manual Requote | |

Profile Parameters

| Days to Expiration | 30 |
|---|---|
| Price Units | Ticks |
| Bid Offset | 2 |
| Bid Quantity | 1 |
| Bid Reserve Offset | 3 |
| Bid Reserve Qty | 1 |
| Ask Offset | 2 |
| Ask Quantity | 1 |
| Ask Reserve Offset | 3 |
| Ask Reserve Qty | 1 |
| Cover Order Offset | 2 |

Quoting Limits

| Maximum Position | |
|---|---|
| Bid Change Allowance | |
| Ask Change Allowance | |
| If Quote In, Join Mkt | ☐ |
| If Quote Out, Join Mkt | ☐ |
| Don't Cross Market | ☐ |
| Market Improve Limit | |
| Quote Move Limit | |
| Stale Quote Timeout | |

Close

FIG. 11

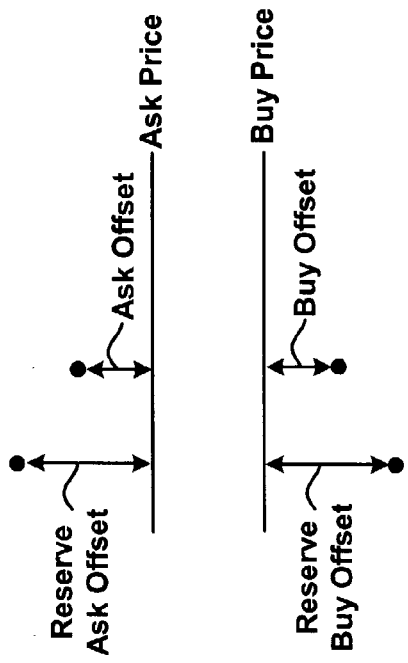
FIG. 12
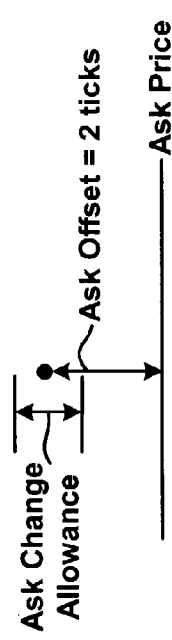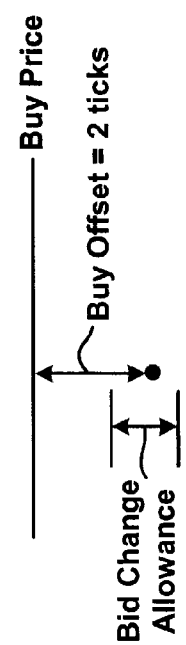
FIG. 13

FIG. 16

Profiles

[812]

Name [810]

[ New 804 ] [ Save 806 ] [ Delete 802 ]

{ 822 }

| Account | ABC | |
|---|---|---|
| Profile Base Price | Market | |
| Throttle Quoting | ☐ | 500 Millisecs between Quotes |
| Enable Cover Orders | ☐ | Cover Order Color |
| Manual Requote | | |

Profile Parameters { 820 }

→ 824

| Name | White | Red | Green | Blue | Orange | Copper |
|---|---|---|---|---|---|---|
| Days to Expiration | 30 | | | | | |
| Price Units | Ticks | | | | | |
| Bid Offset | 2 | | | | | |
| Bid Quantity | 1 | | | | | |
| Bid Reserve Offset | 3 | | | | | |
| Bid Reserve Qty | 1 | | | | | |
| Ask Offset | 2 | | | | | |
| Ask Quantity | 1 | | | | | |
| Ask Reserve Offset | 3 | | | | | |
| Ask Reserve Qty | 1 | | | | | |
| Cover Order Offset | 2 | | | | | |

Quoting Limits

| Maximum Position | | | | | | |
|---|---|---|---|---|---|---|
| Bid Change Allowance | ☐ --- | ☐ | ☐ | ☐ | ☐ | ☐ |
| Ask Change Allowance | | | | | | |
| Stale Quote Timeout | ☐ --- | ☐ | ☐ | ☐ | ☐ | ☐ |

[ Close ]

800 ↗

SYSTEM AND METHOD FOR AUTOMATED TRADING

RELATED PATENT APPLICATIONS

The present application claims priority to U.S. Provisional Application No. 60/389,794 entitled "A System and Method for Automated Trading," which was filed Jun. 19, 2002.

FIELD OF THE INVENTION

The present invention is generally directed to electronic trading, and in particular, facilitates trading of any tradeable object in an electronic trading environment.

BACKGROUND

Trading methods have evolved from a manually intensive process to a technology enabled, electronic platform. Advances in technology are having an increasingly large and broad impact on trading and the way in which exchanges conduct business. What was previously seen as just a supplement to the traditional pit trading, electronic trading platforms continue to increase in importance and popularity. The advent of electronic trading has meant that a customer can be in virtually direct contact with the market, from practically anywhere in the world, performing near real-time transactions, and without the need to make personal contact with a broker. Electronic trading systems are also convenient for floor brokers on the floor at an exchange for receiving orders electronically.

Exchanges that support electronic trading are generally based on a host, one or more computer networks, and clients. In general, the host includes one or more centralized computers to form the electronic heart. Its operations typically include order matching, maintaining order books and positions, price information, and managing and updating a database that records such information. The host is also equipped with an external interface that maintains uninterrupted contact to the clients and possibly other trading-related systems.

Typically, market participants link to the host through one or more networks. A network is a group of two or more computers linked together. There are many types of networks such as local area networks and wide area networks. Networks can also be characterized by topology, protocol, and architecture. However, any type of network configuration can be used in electronic trading. For example, some market participants may link to the host through a direct connection such as a T1 or ISDN. Some participants may link to the exchange through direct connections and through other common network components such as high-speed servers, routers, and gateways, and so on. For example, the Internet can be used to establish a connection between the client and the host. There are many different types of networks, and combinations of network types, known in the art that can link market participants to the host.

Regardless of the way in which a connection is established, software running on the clients allows people to log onto one or more exchanges and participate in one or more markets. A client is a computer that accesses one or more networks. For example, a client can be a personal computer, laptop computer, hand-held computer, and so on. Some clients run software that creates specialized interactive trading screens. In general, the trading screens enable people to enter orders into the market, obtain market quotes, and monitor positions. The range and quality of features available varies according to the specific software application being run.

Sometimes traders also use a separate spreadsheet program or another similar program to receive market data feeds and to generate numbers, based on those feeds, which the traders can use to determine whether to buy and/or sell tradeable objects. Then, in response to the generated numbers, the trader can manually enter and execute orders into a trading application. Instead of manual order entry, some traders use a more brute force approach with often limited flexibility by linking a spreadsheet program directly to a trading application. Orders are then automatically entered and executed by the trading application based on the generated numbers. Use of spreadsheets and trading applications in this manner does allow traders to enter orders faster than using traditional methods of order entry and execution. However, to profit in today's rapidly moving markets, traders must be able to react more quickly and assimilate an enormous amount of data. For example, a trader may have to assimilate market data, world news, business news, and so on before making trades. Consequently, a skilled trader with even the quickest software, the fastest communications, and the most sophisticated analysis can significantly improve the trader's own or the trader's firm's bottom line. The slightest advantage in speed or ability to assimilate information can generate significant returns in a fast moving market. Therefore, in today's fast and dynamically changing markets, a trader lacking a technologically advanced interface is at a severe competitive disadvantage. Prior use of such programs is still an inadequate solution to handle the dynamics of such a fast moving market.

It is therefore desirable for electronic trading systems to offer tools that can assist a trader in adapting his or her strategy to an electronic marketplace, and help the trader to make trades at desirable prices.

BRIEF DESCRIPTION OF THE DRAWINGS

FIGS. 4-6 illustrates an example interface to a preferred embodiment of an automated trader;

FIG. 8 illustrates an example market grid window for selecting the tradeable objects to trade using a preferred embodiment of the automated trader;

FIG. 9 illustrates an example use of the visual indicator as might be seen in an example interface of FIG. 4;

FIG. 10 illustrates another example use of the status light indicator as might be seen in a trading application interface window;

FIG. 11 illustrates an example profile setup window as used by a preferred embodiment of the automated trader to view, create, edit, and/or change profiles;

FIG. 12 is a graphical illustration of ask, buy, and reserve order offsets;

FIG. 13 is a graphical illustration of ask and bid allowances;

FIG. 16 illustrates another example of a profile setup window.

DETAILED DESCRIPTION

General Overview

Figure 1:
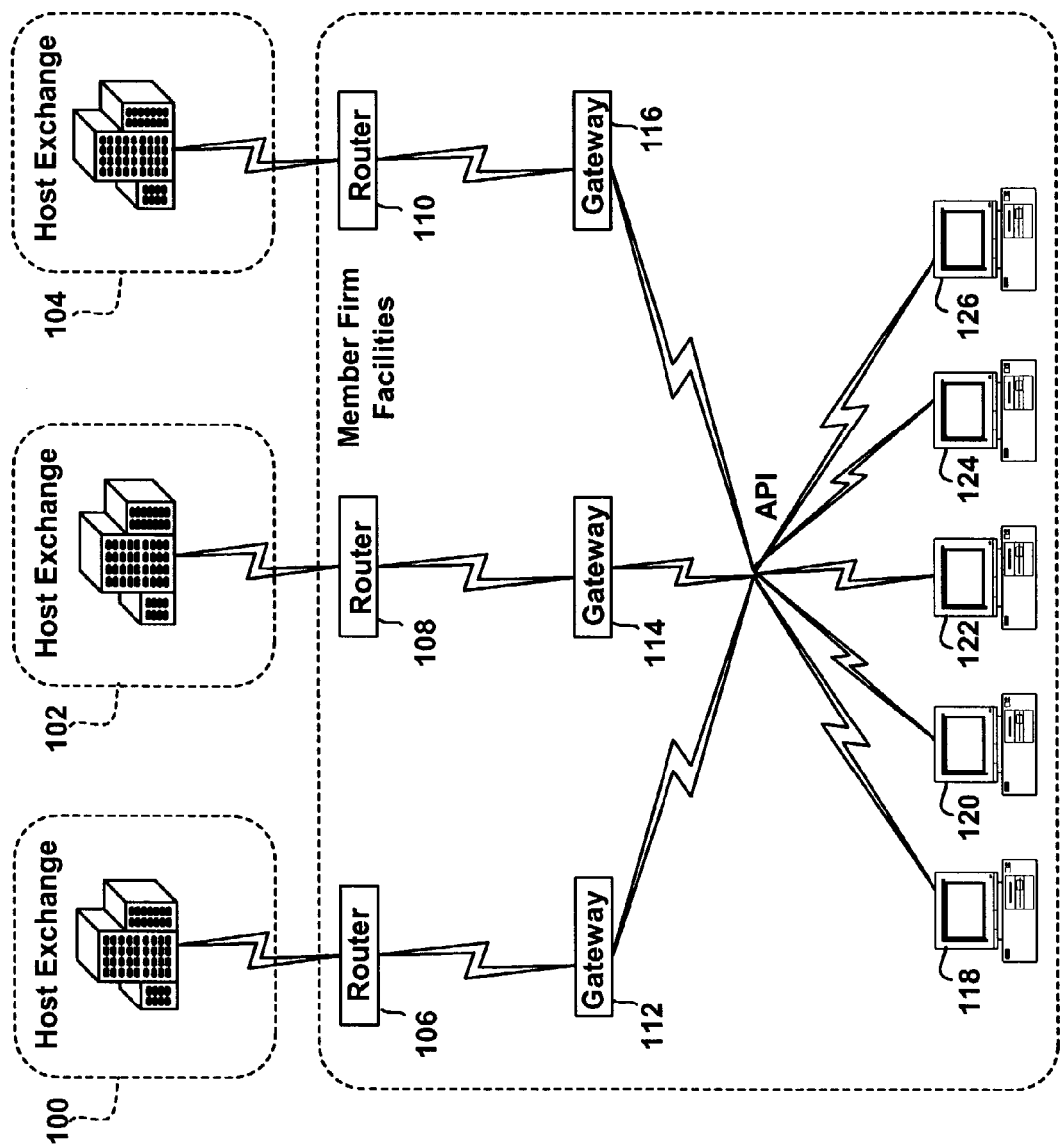
FIG. 1 illustrates an example network configuration between multiple exchanges and client sites on which the present embodiments may be implemented.

The preferred embodiments, generally referred to herein as the "automated trader," are provided to facilitate the buying and/or selling of tradeable objects. According to one preferred embodiment, the automated trader implements a user programmable interface. The user programmable interface allows a user to simply develop a program (e.g., trading strategy) that is based on a set of specifications and/or relationships given by the user and input into a profile, or if desired, input directly into the programmable interface referred to as direct entry. The automated trader can be programmed to automate the entire transaction and management process, or the automated trader can be programmed to only assist the user in trading, whichever is desired. As used herein, a transaction includes any type of discrete activity such as an entry of an order, request to delete an order, entry of a quote, request to cancel and replace, and so on, however each of these terms and the variations (e.g., transactions, orders, quotes, etc.) may be used interchangeably unless otherwise indicated.

Referring first to a profile. Preferably, the profile simplifies program creation by providing a set of profile parameters that can assist the user in characterizing his or her particular trading strategy. The user can create as many profiles as needed to accommodate any number of trading strategies. For each tradeable object and/or market situation, a profile may be dynamically selected, and then the automated trader can execute the program to perform a series of actions according to that selected profile (and directed order entry, if any). The profile can be selected manually by the user or automatically based on market conditions. According to a preferred embodiment, the user can change profiles at any time such as before trading or on the fly (i.e., when the automated trader is on). Moreover, when trading with a particular profile, the user can alter one or more profile parameters on the fly. As a result of the automated trader's programmable flexibility, the user can, for example, focus on his or her trading strategy while the automated trader is executing its program, which might include order entry and execution.

In addition to programming the automated trader through a profile, the user can also program it through use of direct entry. Preferably, direct entry allows the user to enter numeric values or formulas, which might include mathematical statements that describe the actions to be performed on numeric values, directly into the user programmable interface. According to a preferred embodiment, the automated trader is programmed by the combination of the profile and direct entry, but alternatively, it can be programmed by only direct entry or by only the profile.

As briefly mentioned above, the automated trader accepts formulas in the profile and in direct entry embodiments. Regardless of where the formulas are entered (e.g., the profile or through direct entry) the automated trader will preferably incorporate these formulas into its calculations, if programmed to do so. Formulas can also be linked from a spreadsheet or other known analysis tool.

Because in a preferred embodiment the automated trader is capable of accepting instructions for performing a task or an operation, it can assist the user in performing any trade related tasks. For example, as part of the user's strategy, the automated trader can be programmed to automatically enter orders into the market. In this example, the automated trader can be programmed to trade, based on the user's profile, in a complete and automatic fashion, if the user so desires. That way, for example, the user can spend more time on developing his or her strategy rather than manually implementing it.

If the user wants to play a more active role in the execution of his or her trading strategy, but still would like some assistance, then preferably the automated trader can be programmed only to assist the user. For example, the automated trader can be programmed to assist the user in determining prices, referred to herein as suggested prices, at which orders may be entered into the market. The user can trade according to the suggested prices or the user can trade separately from them, whichever the user desires. In another example, the automated trader can be programmed to utilize indicators to relay information to the user. Indicators can be used to indicate the suggested prices to the user in the automated trader, or alternatively, the indicators can be exported to another trading related application and used to indicate the suggested prices in that application.

The automated trader can be programmed in various other ways. For instance, some examples describe how the automated trader can be easily programmed to automatically implement cover orders. This is useful because sometimes a user might want an offsetting order to be sent directly into the market to offset a previous position. Some examples describe how the automated trader can also be programmed to place certain limits on the user's trading, and how the system acts accordingly. This is helpful because it can reduce the number of transactions, such as orders, quotes, delete order requests, cancel/replace requests, etc., unnecessarily entered into the market, especially when markets are undergoing periods of extreme volatility. By reducing the number of transactions entered into the market, the user may avoid extra fees often associated with exceeding transaction limits placed by an exchange. For example, an exchange might have an order limit, quoting limit, and so on. Furthermore, the automated trader can also reduce or prevent losses in the market by examining the validity of prices of possible orders before they are actually placed into the market. These examples and others relating to how the automated trader can be programmed are described below.

Aspects of the automated trader will become readily apparent to one skilled in the art from the following description. Furthermore, there are many advantages to the automated trader, too numerous to mention here, but which will also become apparent with the following description. One advantage, however, is that the automated trader can execute its program in an extremely fast speed, even faster than the traditional manual methods of analyzing data, entering orders through an input device (e.g., a mouse, keyboard, etc.), and so on. Another advantage is that the automated trader helps the user assimilate large amounts of data to assist the user in his or her trading. Yet another advantage is that user can easily and flexibly program the automated trader, at any time before or during actual trading, to implement his or her trading strategy.

It should be noted that, the term "tradeable objects," as used herein, refers simply to anything that can be traded with a quantity and/or price. It includes, but is not limited to, all types of tradeable objects such as financial products, which can include, for example, stocks, options, bonds, futures, currency, and warrants, as well as funds, derivatives and collections of the foregoing, and all types of commodities, such as grains, energy, and metals. The tradeable object may be "real", such as products that are listed by an exchange for trading, or "synthetic", such as a combination of real products that is created by the user. A tradeable object could actually be a combination of other tradeable object, such as a class of tradeable objects.

Example Network Configuration

The automated trader may be implemented in any type of electronic trading environment. One such suitable environment is described in U.S. patent application Ser. No. 09/590, 692, filed Jun. 9, 2000, entitled "Click Based Trading with Intuitive Grid Display of Market," and is also described in U.S. patent application Ser. No. 09/589,751, filed Jun. 9, 2000, entitled "Clicked Based Trading with Market Depth Display," the contents of both applications are incorporated herein by reference. However, it should be understood that the automated trader of the preferred embodiment is not limited to any particular network architecture or trading application, but rather may be applied with utility on any client device in any network that can be used for electronic trading. Furthermore, the present invention is not limited to a completely electronic trading environment where orders are sent to an electronic matching engine. For example, the present invention could be utilized with an electronic trading application that sends orders electronically to a terminal where a person (e.g., a floor broker) executes those orders in a traditional open-outcry trading floor.

FIG. 1 shows an example system substantially similar to the one described in the above incorporated patent applications. The electronic trading system may be configured to allow for trading in a single or in multiple exchanges simultaneously. This illustration shows multiple host exchanges 100-104 connected through routers 106-110 to gateways 112-116. The host exchanges may include Electronic Communication Networks (ECNs) like Island, which is a well-known electronic trading facility. Other host exchanges may include the Chicago Mercantile Exchange (CME), the Xetra (a German stock exchange), and the European derivatives market (Eurex). Multiple client terminals 118-126 for use as trading stations can then trade in the multiple exchanges through their connection to the gateways 112-116.

When an electronic trading system is configured to receive data from multiple exchanges, it is preferable to translate the data from each exchange into a format that may be used by a trading application and/or displayed using a graphical user interface. For the example system shown in FIG. 1, an application program interface ("API") translates the incoming data formats from the different exchanges 100-104 to a common data format. This translation function of a preferred embodiment may be disposed anywhere in the network, for example, at the gateway server, at the individual workstations or at both. In addition, storage elements at the gateway servers, the client workstations, and/or other external storage may cache, buffer, or store historical data, such as order books that list the user's active orders in the market; for example, those orders that have neither been filled nor cancelled. Information from different exchanges can be displayed in one or in multiple windows at the client workstation. While reference is made through the remainder of the specification to a single exchange to which a trading terminal is connected, the scope of the invention includes the ability to trade, in accordance with the trading methods described herein, in multiple exchanges using a single trading terminal.

Example Client Device

Figure 2:
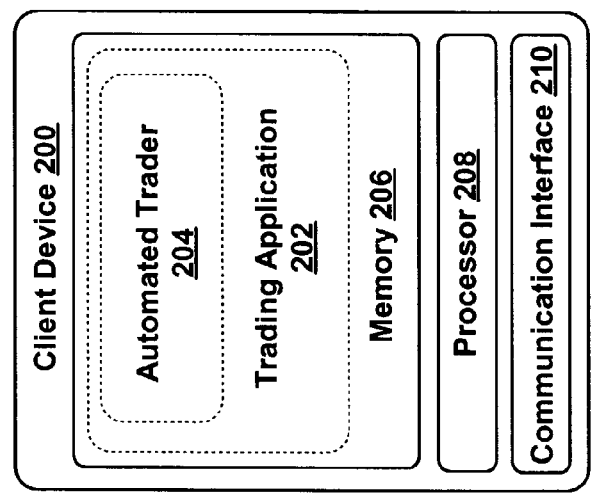
FIG. 2 illustrates an example software architecture of a preferred embodiment of an automated trader and a client device.

FIG. 2 shows an example software architecture of a preferred embodiment of an automated trader 204 and a client device 200. Also included in the figure is a trading application 202. In this example, the automated trader 204 and the trading application 202 may share commonly used information. The client device 200 is preferably a computer that is connected to one or more exchanges in a manner similar to that system illustrated in FIG. 1. The client device 200 preferably has a communication interface 210 that allows the client device 200 to communicate either directly or indirectly (using intermediate devices) with one or more exchanges to receive and transmit market, tradeable object, and trading order information. The client device 200 is able to interact with the trader and to generate contents and characteristics of a trade order to be sent to the exchange. Preferably, the trading application 202 allows for a trader to view market data, enter and cancel trade orders and/or view orders. A commercially available trading application that allows a user to trade in a system like that shown in FIG. 1 is X_TRADER® from Trading Technologies International, Inc. of Chicago, Ill. X_TRADER® also provides an electronic trading interface, referred to as MD Trader™, in which working orders and/or bid and ask quantities are displayed in association with a static price axis or scale. As mentioned above, the scope of the present invention is not limited by the type of terminal or device used, and is not limited to any particular type of trading application. For example, the client device could be a hand-held device, personal computer, laptop, workstation, and so on. As known to those skilled in the art, these devices include at least one processor 206 and at least one memory device 208. The processor may be a microprocessor, a micro-controller, or any device, which performs arithmetic, logic or control operations, and the memory devices may be a volatile or non-volatile memory, for example.

In an alternative embodiment, the automated trader is a separate and independent software application from the trading application. In this alternative embodiment, the automated trader does not necessarily interact with the trading application. Therefore, the need for an additional trading application is not necessary for the automated trader to perform its function described herein. However, if the trading application is installed on the client device, it is possible for the automated trader to interact with it, such as by sharing any type of commonly used information (e.g., as described in the embodiment above).

According to this alternative embodiment, the automated trader's functionality can be implemented anywhere. For example, some or all of the functionality of the automated trader can be implemented at the communications interface 210. That is, many of the functions of the automated trader described herein can be implemented at the communications interface 210 to operate as an intelligent communications interface between one or more third-party software applications and one or more exchanges.

In another embodiment, the automated trader is installed at a server and/or gateway, rather than at the client device. In this embodiment, the client device can access the automated trader over a computer network. In a similar embodiment, the automated trader is partially installed on the server and/or gateway and the remaining portion of the automated trader is installed on the client device. Separating the software and the tasks associated with it onto different computers may be especially useful when the client device has little processing power (e.g., a handheld device). Of course, there are many other alternatives known by one skilled in the art in which the automated trader may be installed and/or accessed by the user.

Implementing a Preferred Embodiment of an Automated Trader

In a preferred embodiment, an automated trader incorporates a user programmable interface that allows the user to develop a program to implement a trading strategy that is based on a set of specifications and/or relationships given by the user. The user programmable interface may include any type of interface that allows the user to communicate with the automated trader. One example of a user programmable interface is a command-driven interface. Another example of a user programmable interface is a graphical user interface that takes advantage of computer graphics. The graphical user interface may include one or more windows that can be moved around the display screen, and their size and shape can be changed at will. A window might include icons that represent commands, files, or more windows. Of course, the present invention can use other types of user programmable interfaces, or alternatively, the present invention does not utilize a programmable interface of this type at all, such as in the intelligent communications interface embodiment. For example, in the intelligent communications interface embodiment, a third-party application would simply input one or more variables into the automated trader, such that orders are placed into the market based on those variables.

Figure 3:
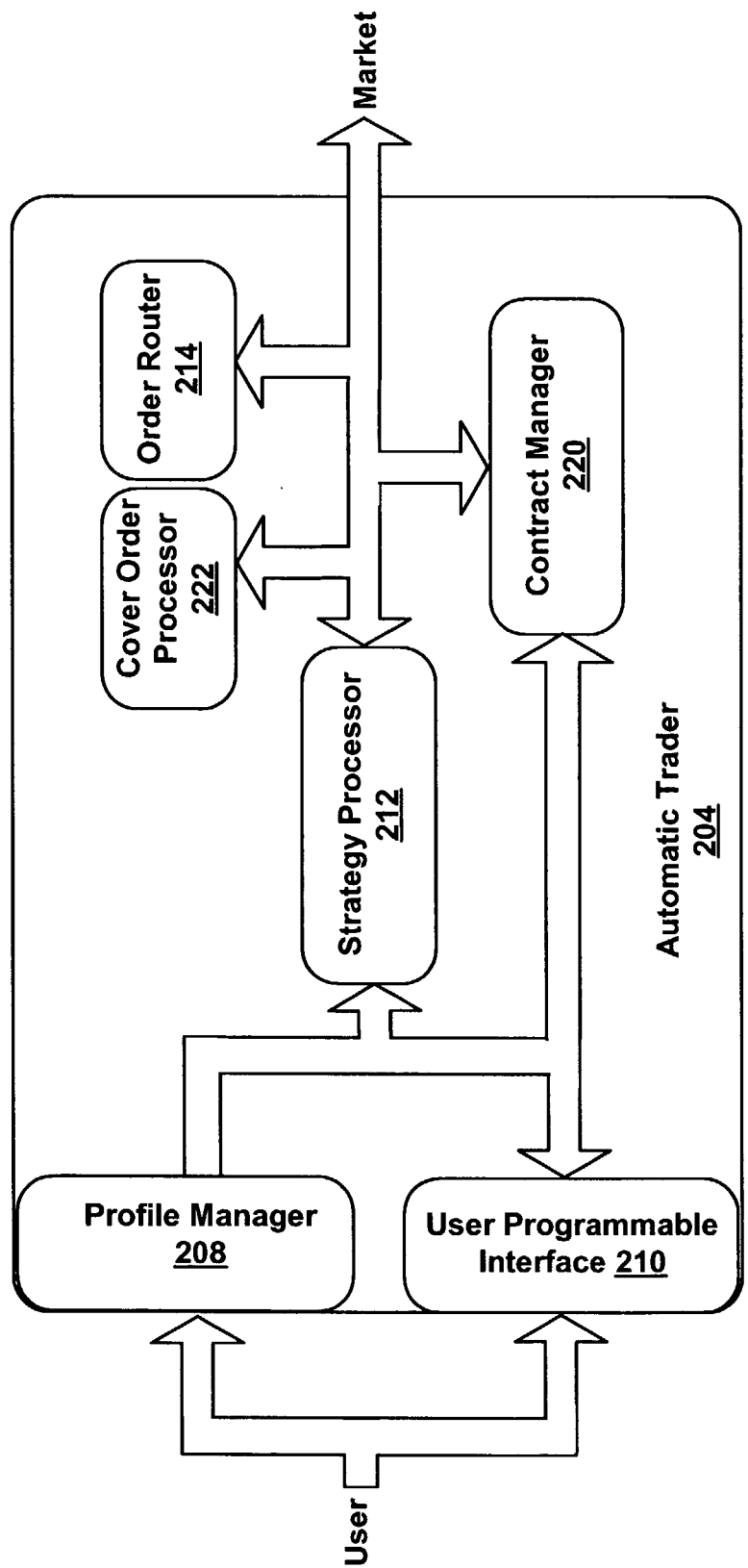
FIG. 3 illustrates an example software architecture of a preferred embodiment of an automated trader.

Referring to FIG. 3, in a preferred embodiment, the user programmable interface 210 is implemented in a software module or processor, referred to generally as a user programmable interface module. The user programmable interface 210 can be a routine and/or data structure (or collection of routines and/or data structures) stored in memory that performs the function of the user programmable interface described herein. As known in the art, modules such as the user programmable module 210 can be connected together with other modules to form the collective system of an automated trader. Alternatively, one skilled in the art can instead use an integrated architecture, in which no clear divisions exist between components, or where a combination of modular and integrated architecture exists.

Figures 6, 8:
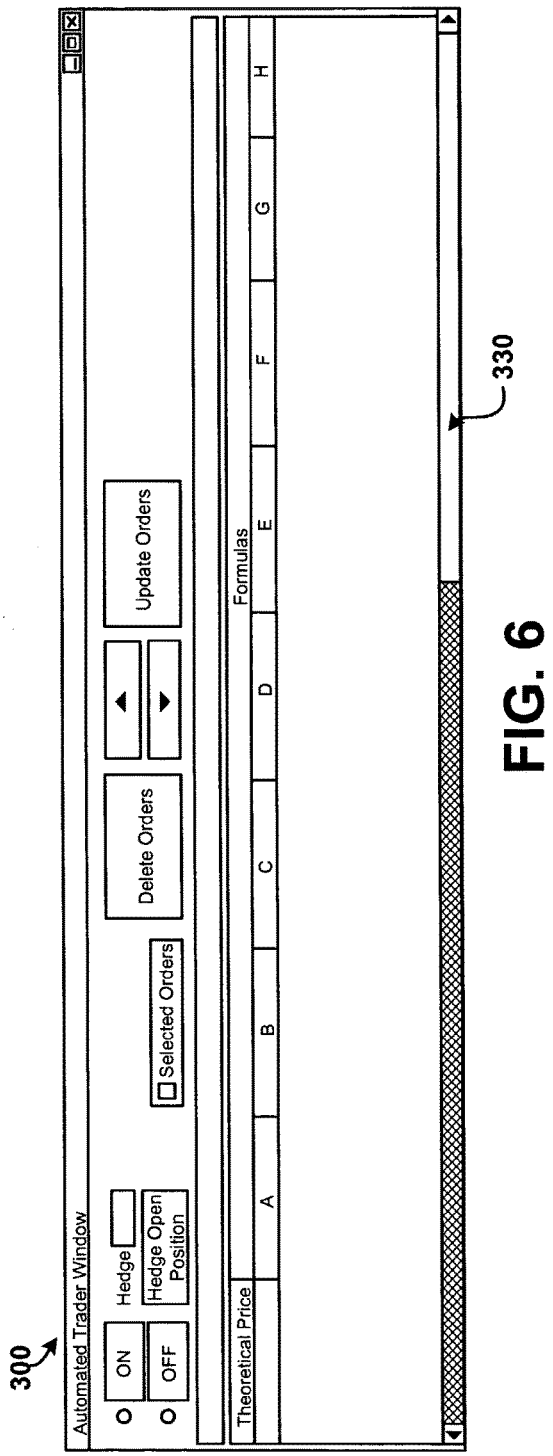

FIGS. 4-6 show one example of a user programmable interface of a preferred embodiment. In this example, the user programmable interface is referred to as an automated trader window 300, which might be displayed on a screen of a client device. According to this embodiment, the automated trader window 300 may be implemented on a grid created from a software package such as Stingray® from Rogue Wave® of Boulder, Colo., which is a commercially available product that forms a spreadsheet like grid of rows and columns that intersect to form cells.

In this example, the automatic trading window 300 is used to provide the user with a simple way to program the automated trader by supporting both direct entry and profile creation. To accommodate this functionality, and/or any other desired functionality, the automated trader window 300 can include as many functional icons as the user requests, where an icon is a small (or large) image displayed on the screen to represent an element that can be manipulated by the user. Some example icons are shown in FIGS. 4-6 and are generally introduced below. It should be understood, however, that the preferred embodiment is not limited to the number of icons present in the figures, nor are they limited to the example layout also shown in the Figures. Furthermore, the automated trader window 300 might be configured in a variety of different ways according to the user's preference, most of which are not illustrated for sake of clarity.

To begin use of the automated trader, a user may select the "ON" icon to turn on the automated trader. Preferably, the automated trader, by default, enters into a manual mode. Preferably, at any time, the user can switch the automated trader from the manual mode into the automatic mode, if so desired. The manual mode and automatic mode are both described below, but in general, when the automated trader is in manual mode the user has to select the "Update Orders" icon to enter orders into the market. If desired, the automated trader can, by default, enter into the automatic mode. Selecting the "OFF" icon turns the automated trader off. Once the automated trader is turned off, the orders in the market are preferably deleted by sending one or more delete transaction messages to the appropriate exchanges.

Next to the "OFF" icon is the "Hedge Open Position" icon. In a preferred embodiment, the "Hedge Open Position" icon provides a feature that allows a user to manually adjust his or her open position by an amount given in hedge field 302. In another embodiment, the "Hedge Open Position" icon allows the automated trader to automatically adjust the user's open position, by an amount given by the user, by hedging into other markets. In yet another embodiment, the automated trader can be programmed to reduce the user's open position based on a hedged position in other products. The function of the "Hedge Open Position" icon is described more below.

When selected, the "Delete Orders" icon deletes (or attempts to delete) working orders from the market for all tradeable objects shown in window 300. The "Update Orders" icon, when selected, immediately enters orders into the market for all of the tradeable objects shown in window 300 at the price and quantity shown in their respective scratch pad cells (e.g., under the "Scratch" column, which is described below). When the "Selected Orders" box 304 is selected, it allows the user to use the "Delete Orders" icon and the "Update Orders" icon only for those tradeable objects which have been selected and highlighted in the window 300. Other means of selection, in addition to highlighting, which are known in the art, may also be used.

Preferably, tradeable objects can be added to the automated trader window 300 by selecting them using a selection means from a market window onto the automatic trade window 300. Selection means, as used herein, includes menu-driven mechanisms (i.e., pull-down menus, drop-down menus, pop-up menus, and so on.), command line entry mechanisms, check boxes used to enable or disable one or more features or options, drag-and-drop, and other known methods of selection.

Referring back to FIG. 3, in a preferred embodiment, a contract manager 220 is implemented in a software module or processor to control the selection of the tradeable objects to be managed by the automated trader 204. Moreover, the contract manager 220 can control the selection and insertion of the contracts into the grid as well as the updating of market and other types of data.

FIG. 8 shows an example of a market window 700. The market window 700 lists those tradeable objects (e.g., contracts) from exchanges in which the user has logged onto. The tradeable object name is given in the "Contract" column. Although it is not necessary, information for each tradeable object may also be displayed in the market window 700. For example, the market window 700 provides columns of the working buys ("WrkBuys"), bid quantity ("BidQty"), bid price ("BidPrc"), ask quantity ("AskQty"), ask price ("AskPrc"), and working sells ("WrkSells"). The market window 700 is just one example of a market window, but there are many other similar types of market windows with more or fewer items of interest that could be used instead.

Tradeable objects can also be added to the automated trader window 300 by other mechanisms besides selecting them from a market window. In one alternative embodiment, the automated trader window 300 employs a command-driven system, in which the user explicitly enters the name of the tradeable object. In another embodiment, the user can choose a tradeable object from a menu by highlighting it and then pressing the Enter key, or by simply pointing to the item with a mouse and clicking on one of the mouse buttons. Or alternatively, drag-and-drop can be used to add tradeable objects to the automated trader window 300.

Turning back to FIG. 4, preferably, the automated trader window 300 includes a section 314 that displays information associated with the tradeable objects selected. In one embodiment, the section 314 utilizes a grid, which is divided into columns and rows that intersect to form cells, such as example cells 316-326 shown in the Figure for illustration. Preferably, each cell can be uniquely identified and each cell can hold text, a value, or a formula. Moreover, the user can input information in the form of numbers and formulas into section 314. According to this example, each column is labeled at the top and information in each row corresponds to one tradeable object. Various kinds of information are displayed in section 314, each of which is described below with respect to the particular columns. The user can use the information displayed in section 314 or the user can input information into section 314 in many different ways other than what is described herein, therefore it should be understood that the present invention is not necessarily limited to displaying or inputting the information in the particular way described below.

Section 314 provides a "Status" column (e.g., cells 316, 318, 320, etc.) that provides a visual indicator that can be programmed to signify, among other things, the status of the automated trader, and can also serve to indicate to the user when to take action. The indicator can be visual to include text, flashing lights, colors, and/or audible such as sounds, or any combination of visual and audible. FIGS. 9 and 10 show two example embodiments where color (or a variation of color) is used as a visual indicator.

FIG. 9 shows an embodiment where the visual indicator is a status light displayed in a preferred embodiment of the automated trader window 300 of FIG. 4. In this embodiment, status lights 802 and 804 are located in cells 316 and 318, respectively. In one aspect of the embodiment, when the automated trader is in manual mode, the status light (for example, status lights 802 or 804) turns a designated color to indicate that the automated trader is in the process of calculating values, the market conditions have not changed enough to enter another order, the user has reached their maximum position, and/or some other programmed reason. The status light (for example, status lights 802 or 804) turns a designated color to suggest when an order at a suggested price may be entered into the market. Based on the color of the status light in manual mode, the user can enter orders into the market by simply selecting the "Update Orders" icon.

In another aspect of the embodiment, when the automated trader is in automatic mode, the status light can be programmed to indicate different things than when the automated trader is in manual mode. To illustrate, assume that status lights 802 and 804 include other colors such as "green," "red," and "yellow" (all colors are configurable). Then, according to this example, a green status light might indicate that the automated trader is performing transactions with an exchange. For instance, the automated trader is automatically updating and entering the orders into the market. A red status light might indicate that the automated trader has stopped entering orders into the market. For instance, the automated trader might stop entering orders into the market because the trading limits have been reached, trading is not occurring in the market, or the connection to the market has been lost. A yellow status light might indicate that other conditions have occurred such as trading has temporarily paused because of throttling (throttling is described more below) or the suggested trades are within other trading limits. Regardless of the type of indicator used, in a preferred embodiment, based on the indicator, the user can determine what processes the automated trader is currently performing, if any. Of course, the indicators can be programmed to mean different things other than what was described above.

FIG. 10 illustrates another embodiment where an indicator is integrated into another trading application and/or another trading interface (e.g., a third-party trading application and/or interface). To better illustrate this embodiment, a commercially available trading application referred to as X_TRADER® from Trading Technologies International, Inc. of Chicago, Ill. is used to implement the visual indicators. X_TRADER® also provides an electronic trading interface, a portion of which is shown in FIG. 10, referred to as MD Trader™, in which working orders and/or bid and ask quantities are displayed in association with a static price axis scale. The portion shown in FIG. 10 shows a working order column 904 that displays the working orders, a bid quantity column 906 that displays the bid quantities, an ask quantity column 908 that displays the ask quantities, and a price axis 910 that displays the corresponding prices. Although the X_TRADER® trading application is utilized and the MD Trader™ interface is shown in the figure, it should be understood that the preferred embodiments are not limited to any particular trading application and/or trading interface.

In the embodiment shown in FIG. 10, cells, or a portion thereof, within any columns of the trading interface (e.g., cells in columns 904, 908, 910, and 912) can turn a designated color to suggest when and at what price an order should be entered. For example, assume that the automated trader has determined, based on the current market conditions and profile, that the price to submit a sell order is at a price of 106975 and that the price to submit a buy order is at a price of 106850 as shown in the figure. Consequently, according to this embodiment, the automated trader will display a visual indicator in the appropriate cells to indicate this information to the user. In this example, the visual indicators are displayed in the market depth for easy viewing, that is, the cell that contains ask quantity 447 turns a designated color to distinguish itself from the surrounding cells and the cell that contains buy quantity 168 also turns a designated color to distinguish itself from the surrounding cells. Then, for example, when the automated trader is in manual mode, a user can implement the trading strategy, which has been programmed into the automated trader, by simply submitting buy and/or sell orders at the suggested prices levels. When the automated trader is in automatic mode, the user can simply watch the automated trader implement his or her trading strategy in the trading interface. There are many other ways in which the user can utilize the visual indicators in this embodiment; for example, a separate column 912 can be used to indicate when and where to enter orders. Indicators such as visual and/or audible indicators can be implemented anywhere on a trading interface so long as the user is aware of the location and its purpose.

Referring back to FIG. 4, the "Active" column allows a user to activate or start trading a tradeable object of a particular row. In one embodiment, a selection means is provided in a cell that allows the user to actively trade the tradeable object corresponding to the row of the cell. Conversely, the user can stop trading the tradeable object by using the same selection means (or a different selection means) to inactivate trading for that row.

The "Contract" column indicates the current name of the tradeable object for each row. The tradeable object name is the name of the tradeable object given by the exchange, but alternatively, the user can rename the tradeable object to suit his or her particular need.

Control parameters under the "Control" column give the user the flexibility to change the operation of the automated trader from manual mode to automatic mode, and vice-versa, change the current profile (before trading or on the fly), and change the account name.

Preferably, the automated trader gives the user flexibility in determining whether the automated trader enters calculated orders into the market automatically or through manual intervention by the user. In one embodiment, each cell under the "Manual" column utilizes a selection means to change the operation of the automated trader into manual mode. Likewise, each cell under the "Automatic" column utilizes a selection means to change the operation of the automated trader into automatic mode. In this embodiment, preferably only one mode (i.e., manual or automatic) may be selected at any time for each row, but that the mode may be dynamically changed at any time. It should be understood that even in manual mode, the automated trader may still perform some automatic operations (e.g., automatically calculating suggested prices in the scratch pad, etc.), of course, this depends on how it is programmed.

As previously mentioned, the user can program the automated trader in many unique ways to characterize any type of trading strategy that he or she might want to implement. One such way is to develop a profile, such that the profile characterizes the user's particular trading strategy. As already mentioned, the user can create as many profiles as needed to accommodate any number of trading strategies. Developing and saving a profile is described in the example illustration section below. In a preferred embodiment, a profile may be selected for each tradeable object. Preferably, the user can change profiles at any time before or while the user is trading. In one embodiment, each cell under the "Profile" column allows the user to select the profile, at any time. In this embodiment, each cell under the "Profile" column utilizes a selection means so that the user can select a saved profile. It is also envisioned that the automated trader can automatically select the profile based on market conditions.

Each tradeable object is preferably associated with an account (or customer). One or more accounts may be added and information corresponding to those accounts can be stored. Then, any trading activity associated with a particular tradeable object is linked to the corresponding account. Through a selection means, the automated trader allows the trader to select the account for each tradeable object in each cell under "Account."

In a preferred embodiment, the automated trader keeps track of the number of transactions a user has for each row, and the displays the number in the cells under the "TransCount" column. Alternatively, the automated trader can keep track of the number of transactions across an account. As previously mentioned, transactions include any type of discrete activity such as an entry of an order, request to delete an order, entry of a quote, request to cancel and replace, etc. Some exchanges impose fines for excessive transactions. If programmed, the automated trader can signal to the user when the transaction level has met an exchange's transaction limit. For example, the automated trader can simply warn the user that the exchange limit has been reached; alternatively, the automated trader can prevent the user from participating in any more transactions. Transaction limits for each exchange can be programmed (or fed into) into the automated trader.

Preferably, the automated trader displays information regarding the user's position in the market and might display the user's net position and open position. As used herein, the net position is the user's current position on the chosen contract for a particular account, and in this embodiment, is the difference between the number of orders bought (a long position) and the number of orders sold (a short position). In other words, if the user has bought 10 more tradeable objects than he or she has sold, this value would be 10. If the same user sold 3 more objects, the net position becomes 7 (i.e., 10−3=7). In another example, if the user has sold 10 more tradeable objects than he or she has bought, the net position would be −10. Then, if the same user bought 3 more objects, then the net position becomes −7 (i.e., −10+3=−7). The user's position is open when the numbers of tradeable objects bought or sold are not equal. The user's position is closed when the numbers of tradeable objects bought or sold are equal.

In a preferred embodiment, cells under the "Position" column display the user's various positions including the user's net and open positions in the market. The "Net" column displays the total net position for a tradeable object for an account. The "Open" column displays the open position for a tradeable object for each row. The open position could be a number based on the user's position at an exchange level, customer level, account level, and so on, depending on how it is programmed. A user may wish to hedge his or her open position into other markets, products, and so on. According to one embodiment, the open position can be manually reduced by using the Hedge Open Position feature. The user can hedge his or her open position by the value in the hedge field 302, such as by selecting the "Hedge Open Position" icon. In one embodiment, the user can manually hedge at any time his or her position elsewhere. In an alternative embodiment, the automatic trader can automatically hedge the user's position in other markets or products based on his or her trading strategy, for example.

Preferably, the automated trader window 300 can display the current market information. Depending on the information an exchange provides, market information may include the inside market, but alternatively may include market depth information. As used herein, the inside market is the lowest sell price (best ask) and the highest buy price (best bid) at a particular point in time. Market depth refers to quantity available at the inside market and can also refer to quantity available at other prices away from the inside market at the same point in time. Market information can contain other types of data such as the last traded price (LTP), the last traded quantity (LTQ), and/or order fill information.

In one embodiment, the columns under the "Market" column display the current market information for each tradeable object. The "MktBidPrice" column shows the market bid price for the corresponding quantity shown in the "MktBidQty" column. The "MktAskPrice" column shows the market ask price for the corresponding quantity shown in the "MktAskQty" column. The "MktLastQty" column shows the last traded quantity in the market, and the "MktLastPrice" column shows the last traded price in the market at that quantity. The "Net Change" column provides the price differential over a period, such as the previous settlement price for each tradeable object.

A horizontal slide bar 330 allows the user to view more columns and row information for each tradeable object. It should be understood, however, that the columns can be arranged in a different order shown in the figures and/or some of the columns can be deleted, if the user desires. Moreover, the names of the columns may be abbreviated so that more information (e.g., more columns) can fit into the viewing area. Although not shown, a vertical slide bar may appear to indicate to the user that more rows of tradeable objects can also be viewed.

Referring to FIG. 5, the slide bar 330 has been moved to view more information. Again, for sake of illustration, the columns are more spaced out more than necessary. To view more information in the automated trader window 300, smaller font size and/or more abbreviations may be used, for example.

Preferably, the automated trader window 300 displays the user's working orders. The cells under the "Working" column display the working orders for each tradeable object. The "WrkBidPrice" column displays the current working bid price, and the "WrkBidQty" column displays the current working bid quantity. The "WrkAskPrice" column displays the current working ask price, and the "WrkAskQty" column displays the current working ask quantity.

Preferably, the automated trader window 300 displays one or more scratch pad areas that operate as temporary storage areas used by a preferred embodiment of the automated trader for displaying calculations, data, and other work in progress. For example, a scratch pad area can show, among other things, information related to suggested orders that, at any time, can be sent into the market automatically (in automatic mode) or manually (in manual mode). The user can use the scratch pad area as a place to monitor and/or change possible order information before an order is actually sent into the market as a working order. The user might also, for example, use the scratch pad to test various strategies, and so forth.

Thus, in a preferred embodiment, columns under the "Scratch" column form a scratch pad area. The "ScrBidQty" column displays the scratch bid quantity, and the "ScrBidPrice" column displays the scratch bid price. The "ScrAskQty" column displays the scratch ask quantity, and the "ScrAskPrice" column displays the scratch ask price. The values placed in the cells of the "ScrBidQty," "ScrBidPrice," "ScrAskQty," and "ScrAskPrice" columns include those that are manually entered by a user (or linked to a manually entered value) and/or calculated and displayed by the automated trader. In a preferred embodiment, a strategy processor calculates values that are placed in the scratch pad area. The values may include numbers (decimal or whole) and/or formulas, if programmed. Examples are provided below.

The columns under the "Profile Parameter" column display some or all of the profile parameters entered by the user and saved in a profile. Preferably, the user can change the parameters shown in window 300 on the fly, but the changed parameters do not necessarily alter the saved profile. That way, the user can quickly change one or more of the parameters without having to access the profile window. Although the parameters are described more below, they might include a "Bid Offset" column that displays the bid offset, a "Bid Qty" column that displays the bid quantity, a "Ask Offset" column that displays the ask offset, a "Ask Qty" column that displays the ask quantity, and a "Max Position" column that displays the maximum position a user can take. In general, the bid offset is a value (positive or negative value) that can be subtracted from the base profile price, to indicate a price at which the user is willing to submit a buy order into the market. The ask offset is a value (positive or negative value) that can be added to the base profile price, to indicate a price at which the user is willing to submit a sell order into the market.

The columns under the "Cover Order" column display information related to cover orders. The "Cover" column displays the cover order offset, and the "Enable" column provides the user with selection means to enable/disable the cover order feature, and also displays whether the cover order option is enabled and/or disabled.

Referring to FIG. 6, the horizontal slide bar 330 again has been moved to view more information. Sometimes a user may wish to trade off a theoretical price (a calculated price other than the market price fed by an exchange). For example, a user may calculate a single theoretical price such that buy and/or sell orders are entered into the market at a price based off the single theoretical price. In another example, a user may calculate bid/ask theoretical prices such that the buy orders are entered into the market at a price based off the bid theoretical and the sell orders are entered into the market at a price based off the sell theoretical. Therefore, if the user has chosen to feed in a theoretical price (e.g., single theoretical, bid theoretical, ask theoretical, etc.) to trade off, the user can input the formula (or link to a spreadsheet with the formula) that calculates the theoretical price in a cell under the "Theoretical Price" column.

One or more columns under the "Formulas" column display formulas that are entered by the user (or linked to a spreadsheet), if any. The formulas establish mathematical relationships between values in the automated trader window and/or in other programs. More columns can be added or columns can be deleted depending on what the user desires.

It should be understood that other columns may also be included or deleted from the window 300, depending on what the user wants to view. Thus, in a preferred embodiment, the user can hide or show columns at his or her discretion. For example, columns that display more profile parameters may be shown or the hedged position for each row may be shown. In another example, columns unique to a tradeable object may also be shown. For example, columns for futures option trading might include "Greeks," which refers to Greek letters that are used in options trading formulas and analysis, which might include delta, gamma, Vega, theta, etc. Therefore, the window 300 is preferably configurable in any fashion so that the user can view the columns of information he or she wishes to view. It should also be understood that the type of information displayed can also be configurable, for example, which fields or icons are displayed.

Aspects of the functionality are described below with respect to the example illustrations. One skilled in the art would appreciate that in a preferred embodiment, the automated trader can be programmed in many ways other than those described herein.

Example Illustration of a Preferred Embodiment of an Automated Trader

As stated earlier, a user can uniquely program the automated trader to suit his or her individual trading strategies. The user can program the automated trader in a variety of different ways and at any time, such as before trading begins or on the fly. Also mentioned earlier, the program is preferably based on a set of specifications and relationships given by the user and input into the profile or input directly into the user programmable interface. Preferably, the automated trader is setup to simplify the task of creating the profile and inputting directly into the user programmable interface. Then, the automated trader can execute the program to perform a series of actions. The following example illustrates one way in which a user might program the automated trader.

Figure 7:
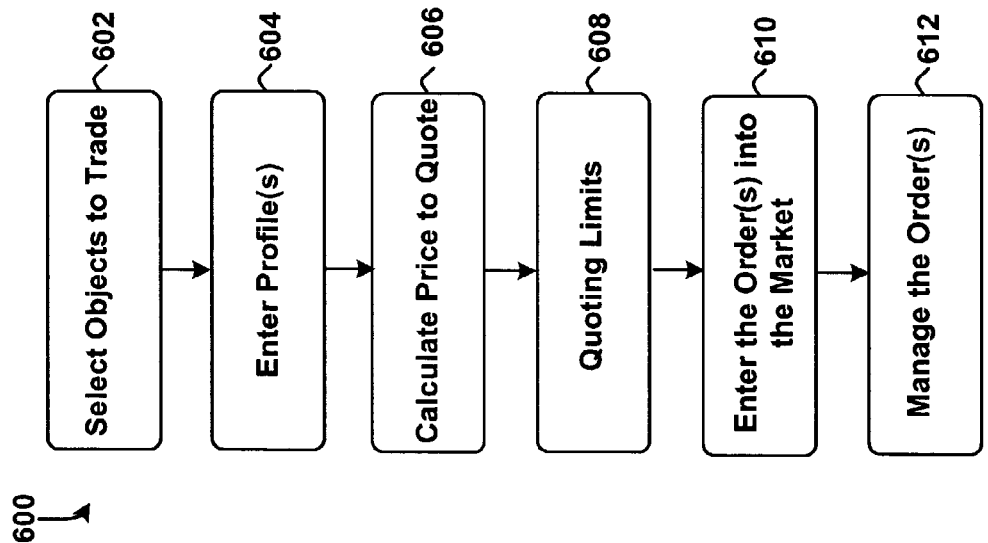
FIG. 7 illustrates an example flow of operation of a preferred embodiment of the automated trader.

FIG. 7 shows a flowchart 600 that, in general, illustrates an example flow of operations performed by the user and a preferred embodiment of an automated trader. The example flow of operations includes selecting one or more tradeable objects at step 602, entering profile(s) for each tradeable object at step 604, calculating a price at which an order is entered at step 606, applying one or more quoting limits at step 608, entering the order into the market, if appropriate at step 610, and managing the order at step 612. Each step of the flowchart 600 is described with respect to their respective sections below. It should be understood, however, that the flowchart 600 provides only an illustrative description, and that more or fewer steps may be included in the flowchart 600, and/or the steps may occur in one or more orders which are different from the order of steps shown in FIG. 7. For example, the step 602 "Select Objects to Trade," may occur before or after the step 604 "Enter Profile(s)." In another example, the step 608 "Quoting Limits," may not be necessary if the user decides not to use them. There are many other alternative examples, too numerous to mention here, that one of ordinary skill in the art would recognize.

At step 602, the user selects one or more tradeable objects from one or more host exchanges. There are many ways in which one or more tradeable objects may be selected for trade. For example, a user may select one or more tradeable objects by highlighting the tradeable object(s) with an input device such as a mouse, keyboard, or touch screen. Upon highlighting the tradeable objects, the user may then drag them into a user programmable interface such as an automated trader window. A user can use any selection means for selecting the tradeable objects.

Using any selection means, for example, one or more tradeable objects can be selected from a market window or any other window that displays tradeable objects. One type of market window that is suitable for selecting tradeable objects is shown in FIG. 8. The market window has a column that lists the tradeable objects (contracts). This example includes tradeable objects "ES JUN02," "ES SEP02," "ES DEC02," "GE JUN02," etc. (some of the tradeable objects are of the same type but have different expiration dates, June, September, and December, however, this is not necessary). Other information associated with each tradeable objects is also displayed in this example market window, such as the inside market and so on, however, it is not necessary to display such information. Nonetheless, one or more objects may be selected from the market window (or a similar window) and dragged into an automated trader window.

Referring back to the flowchart 600, at step 604, one or more profiles are entered. As previously mentioned, the user can create profiles to characterize his or her trading strategy. Profiles provide a way to easily program the automated trader by providing cells (or fields) whereby the user can input information to characterize his or her trading strategy. Profiles may also be saved from a previous use in which the step of creating a profile could be skipped. However, assuming that a profile has not yet been created for purposes of illustration, a user can create a profile by selecting a tradeable object using any selection means and then by selecting the option "Profile Setup."

FIG. 11 shows one example of a profile setup window 800 as a result of selecting the "Profile Setup." The user can create, edit, or delete profiles through a profile setup window like the example window 800 shown in FIG. 11. For example, a user may select to view and/or edit an existing profile by selecting the profile in window 812 (no profiles are shown in window 812). The user may delete an existing profile by selecting the profile in window 800 and pressing the "Delete" icon 802. Moreover, the user may add a new profile by pressing the "New" icon 804, once the profile name is entered in the "Name" field 810. Once the user is finished with the profile setup window 800, he or she may save the profile by selecting save 806, and can select the "Close" icon to close the window 800. Although a profile may be created through other means besides a window (e.g., command line entry, program file, etc.), it should be understood that the profile setup window 800 shown in FIG. 11 is just one example of how a profile window might look if such a window is utilized, and that a suitable profile window might represent more or less information in the same or different manner.

According to this example, a portion of the profile setup window 800 is broken up into columns that intersect with rows to form cells 820. The user can enter information into cells 820 to create or edit a profile. The information that is entered into the cells 820 preferably corresponds to the row titles given in column 822. The row titles shown in column 822 (e.g., the row title "Account" to "Stale Quote Timeout") provide only an example of what might be input by a user to program his or her trading strategy. Therefore, the row titles are not meant to limit the present invention, but rather to illustrate the possibilities in developing a profile. A profile allows a trader to enter values for parameters that are commonly (or uncommonly) used by the trader in establishing a trading strategy. The particular parameters described herein are merely examples of such parameters and a profile could use entirely different parameters. In one embodiment, the software can be programmed to allow a user to create new types of parameters to be used with the profiles.

In this example, the "Account" allows the user to enter and/or select the account name using a selection means. For this example, the account name "ABC" is shown.

According to this example, the "Profile Base Price" allows the user to select which base price is used in calculating prices. For example, using a selection means, the user has the option to choose between "Market Prices," or to create his or her own theoretical price, such as "Single Theoretical," "Bid Theoretical," and "Ask Theoretical." If the user decides to use his or her own theoretical price, one way to incorporate this price in a preferred embodiment is to place a formula (or link to formula) in a cell under the "Theoretical Price" column in FIG. 6. Alternatively, the theoretical price formula (or link) can be placed directly into the profile. In addition, "Direct Entry" may be selected here to allow the user to enter values (i.e., numbers or formulas) directly into one or more scratch pad areas. For this example, the profile base price selected and shown is "Market" for market prices.

In this example, "Throttle Quoting" allows the user to enable throttle quoting (or other transactions, where transactions can includes any type of discrete activity such as an entry of an order, request to delete an order, entry of a quote, request to cancel and replace, and so on). One purpose for throttle quoting can be used to prevent or reduce excess entering of orders and other transactions. Another purpose for throttling transaction messages, such as orders, is to prevent automatic re-pricing of orders during a period of time. In a preferred embodiment, the automated trader continually calculates suggested orders and updates the scratch pad. The throttle-quoting feature is used to throttle the entry of orders from the scratch pad into the market. In an alternative embodiment, throttle quoting can be applied to throttle the calculation of suggested orders by the automated trader. In a preferred embodiment, however, a request to delete an order is always entered into the market, whether or not the throttle-quoting feature is enabled. Furthermore, in a preferred embodiment, cover orders are not throttled. Throttle quoting may be helpful if the markets are moving rapidly and the exchange at which the user is trading charges transaction fees for excessive order entry. To illustrate a type of throttle quoting, the following simple example is provided. Assume that the time period is set to 500 milliseconds. The user, of course, may set any time period. Then, when an order (or some other transaction message) is entered into the market at time t=0, another order (or transaction message) for that tradeable object cannot be entered into the market until time t=500 milliseconds. The system throttles the order (or transaction message) for 500 milliseconds before it is released. Preferably, while the order (or transaction message) is being throttled or held back, the order (or transaction message) can be replaced or updated to reflect more recent order information that might have been generated.

Sometimes a user might want to implement cover orders such that an order is automatically entered into the market to offset his or her previous position. In a preferred embodiment, cover orders are placed directly into the market, thereby bypassing the scratch pad area, but alternatively, the cover order may be first placed into the scratch pad area before being sent out into the market. For example, assume that a user enters a buy order of 10, and the buy order is filled. Then, the automated trader will enter a sell order of 10 into the market to offset the previous buy order of 10. Likewise, if a sell order of 10 is filled, a buy order of 10 is entered into the market. In addition to enabling cover orders, the cover order color can be set in cell 824. Preferable, the cover order color distinguishes cover orders from other working orders that might also be in the market. Other types of visual indicators can be used instead of color or in combination to color.

When "Manual Requote" is enabled, if a user gets filled on a buy or sell order, the automated trader will stop sending orders on the side that was filled until the user presses the "Update Orders" icon, which retriggers automated quoting. For example, if the user's quote is a 10 bid and a 12 offer, then if the 10 bid gets filled, the automated trader will not send in another buy order until "Update Orders" icon is pressed. In this example, however, it will continue to quote the sell side.

The "Days to Expiration" allows an automated trader (or user) to input the days to expiration for a particular tradeable object. For example, an expiration date for a futures contract is referred to as the delivery month. According to this example, the delivery month is the month during which a futures contract expires, and during which delivery may take place according to the terms of the of the contract. Generally, the futures delivery month with the soonest delivery date (or the option delivery month with the soonest expiration date) is referred to as the nearby month. The month which has the latest delivery data is referred to as the far month. Regardless of the type of expiration date, it is preferable that the automated trader can automatically determine the delivery months for a particular tradeable object based on a data feed from the exchange. The tradeable object can have a delivery date given in months (e.g., June, September, and December) or days (e.g., 30 days, 60 days, and 90 days). An alternative embodiment allows the user to manually input the expiration date. For purposes of illustration, FIG. 11 shows 30 days to expiration for the particular tradeable object. It is also possible that the tradeable object doesn't have a particular delivery date or expiration date, and therefore the "Days to Expiration" can be left blank or be programmed not to appear at all.

The "Price Units" allows a user to change the price units for a given tradeable object. By default, the price unit is in ticks, where a tick is the minimum change in a price value that is set by the exchange for each tradeable object. However, other price units might be available such as currency. In this example, the price units are set to "ticks."

As previously mentioned, the "Bid Offset" allows a user to set the desired offset bid price, which represents the price of a buy order that can be entered into the market from the bid price based on the "Profile Base Price." The "Bid Offset" has units given by the "Price Units." The "Bid Quantity" row allows a user to set the quantity a user is willing to trade at the desired offset bid price. Similar to the "Bid Offset," the "Ask offset" allows a user to set the desired offset ask price, which represents the price of a sell order that can be entered into the market, from the ask price set by the "Profile base price." The "Ask Offset" also has units given by the "Price Units." The "Ask Quantity" allows a user to set the quantity a user is willing to trade at the desired offset ask price. FIG. 11, the "Bid Offset" and the "Ask Offset" are both set to 2 ticks from the market. FIG. 12 illustrates a graphical illustration of ask and buy offsets in relation to the inside market (or some other reference price level).

In addition to bid offset and ask offset, a preferred embodiment of the automated trader can be programmed to allow a user to enter a second order (reserve) that is entered into the market when the first order (the buy order at the bid price or the sell order at the ask price) is filled. This option allows users to immediately enter another order into the market at a predetermined price and quantity that the user knows has a greater chance of filling because the first order was filled. The "Bid Reserve Offset" allows the user to enter the desired offset, and the "Bid Reserve Qty" allows the user to enter the desired reserve quantity at the reserved offset price. The same is true for the "Ask Reserve Offset" and the "Ask Reserve Quantity," except that they apply to sell orders. Preferably, the reserve ask offset and the reserve buy offset may be set by the user, if desired. The reserve ask offset and the reserve buy offset can have the same value as the ask and/or buy offset or a different value. In the foregoing example and shown in FIG. 11, the "Bid Reserve Offset" and the "Ask Reserve Offset" are both set to 3 ticks from the market. FIG. 12 illustrates a graphical illustration of reserve order offsets in relation to the inside market (or some other reference price level).

Referring back to FIG. 11, the "Cover Order Offset" allows a user to set the offset price for any cover order. For example, if the cover order feature is enabled, then when a buy order of 10 is filled, the automated trader will enter a sell order of 10 into the market at a price 2 ticks above the fill price. Likewise, if a sell order of 10 is filled, then the automated trader will enter a buy order of 10 into the market at a price two ticks below the fill price.

Referring to FIG. 3, in a preferred embodiment, a profile manager 208 provides an interface through which the user can establish, edit, delete, and save profiles that characterize his or her trading strategy. The profile manager 208 can be separate from or the combined with the user programmable interface 210.

Once a profile is entered and saved, the user can preferably select the profile before trading begins or on the fly. Using the example window shown in FIGS. 4-6, the user can, at any time, use any selection means to select a profile in the "Profile" column. By allowing the user to change profiles on the fly, the user can quickly adapt to changing market conditions, or simply the user can quickly and easily test his or her different trading strategies. In addition, according to the preferred embodiment, the user can change the parameters of the profile through the automated trader window 300 by editing cells under the "Profile Parameters" column. In the preferred embodiment, changing the parameters does not necessarily alter the saved profile.

Referring back to FIG. 7, at step 606, the automated trader is programmed to calculate, among other things, the price at which to enter an order/quote into the market. In a preferred embodiment, a strategy processor calculates the price at which to enter orders into the market. In one embodiment, some of the calculated values are then displayed in the cells under the "Scratch" column (shown in FIG. 5), previously referred to as a scratch pad area. Among those values displayed in the scratch pad area include a bid price and bid quantity (under the "ScrBidPrice" and "ScrBidQty" columns, respectively), and an ask price and ask quantity (under the "ScrAskPrice" and "ScrAskQty" columns, respectively). More items of interest, such as the reserve price and quantity or the cover order offset, may also be displayed under the "Scratch" column, if programmed to do so. Furthermore, more than one "Scratch" column can be provided, depending on how it is programmed.

In another embodiment, the user can enter orders directly into the cells under the "Scratch" column, also referred to as direct entry. This embodiment, referred to as the direct entry allows the user to enter numbers, formulas, or link to other numbers/formulas directly into the scratch pad working area. The user can implement direct entry in either the manual or automatic modes.

As previously mentioned, the cells under the "Scratch" column provide the user with a scratch pad area to view suggested order information before orders are actually entered into the market. That way, the user can verify order information calculated by the automated trader, or the user can enter his or her own values directly through direct entry.

At step 608, the automated trader applies any quoting limits, which were programmed into the profile, to the suggested order information in the scratch pad area. Therefore, in addition to providing the user with flexibility on what to quote, the price to quote at, and the quantity to quote, the automated trader window allows input of quoting limits that can be placed on orders before they are entered into the market. According to the example in FIG. 11, the quoting limits include "Maximum Position" row through the "Stale Quote Timeout" row, and can include "Throttle Quoting."

The "Maximum Position" allows the user to set a quoting limit on the user's open position. Once the open position reaches the maximum position, the automated trader is programmed to notify the user that the limit has been reached. The maximum position applies both to the buy side and the sell side. For example, if the buy side reaches the maximum limit and the automated trader is in the automatic mode, then the automated trader will enter only sell orders to reduce the open position. Conversely, if the ask side reaches the maximum limit and the automated trader is in the automatic mode, then the automated trader will enter only buy order s to reduce the open position.

In a preferred embodiment, when the user reaches the maximum position, the automated trader provides the user the option to quickly hedge the open position in full, or partially. According to this preferred embodiment, the user can quickly categorize as hedged his or her open position so that he or she can quickly participate in the market. In one embodiment, a pop-up window is used to allow a user to categorize as hedged his or her open position, but alternatively, any method of indicating this option to hedge may be used.

The "Bid Change Allowance" allows a user to enter an allowance of price units that the user is willing to wait before the automated trader enters another order. Similar to Bid change allowance row, the "Ask Change Allowance" allows a user to enter an allowance of price units, but for the sell side.

FIG. 13 is a graphical illustration of ask and bid allowances in relation to ask and buy offsets. For this graphical illustration, assume that the user enters an order to buy at a bid offset of two ticks. In one embodiment, when the market goes up or down one tick, the automated trader would delete the previous order and re-enter at the market price minus two ticks. In the ask and bid allowance embodiment, with a bid change allowance of one, the automated trader would not necessarily delete the order and re-enter another. Instead, the automated trader keeps the order so long as the market does not move outside of the allowance. So, for example, if the market moves three ticks in one direction, the allowance embodiment would not delete the order (with an offset of two ticks and an allowance of one tick), however, if the market moves four ticks in one direction, the order would be deleted and re-entered at two ticks from the new price. In the former scenario, the market stayed inside the allowance so the order is kept, but in the latter scenario, the market moved outside of the allowance so the order was deleted and re-entered at a new price.

Figures 14, 15:
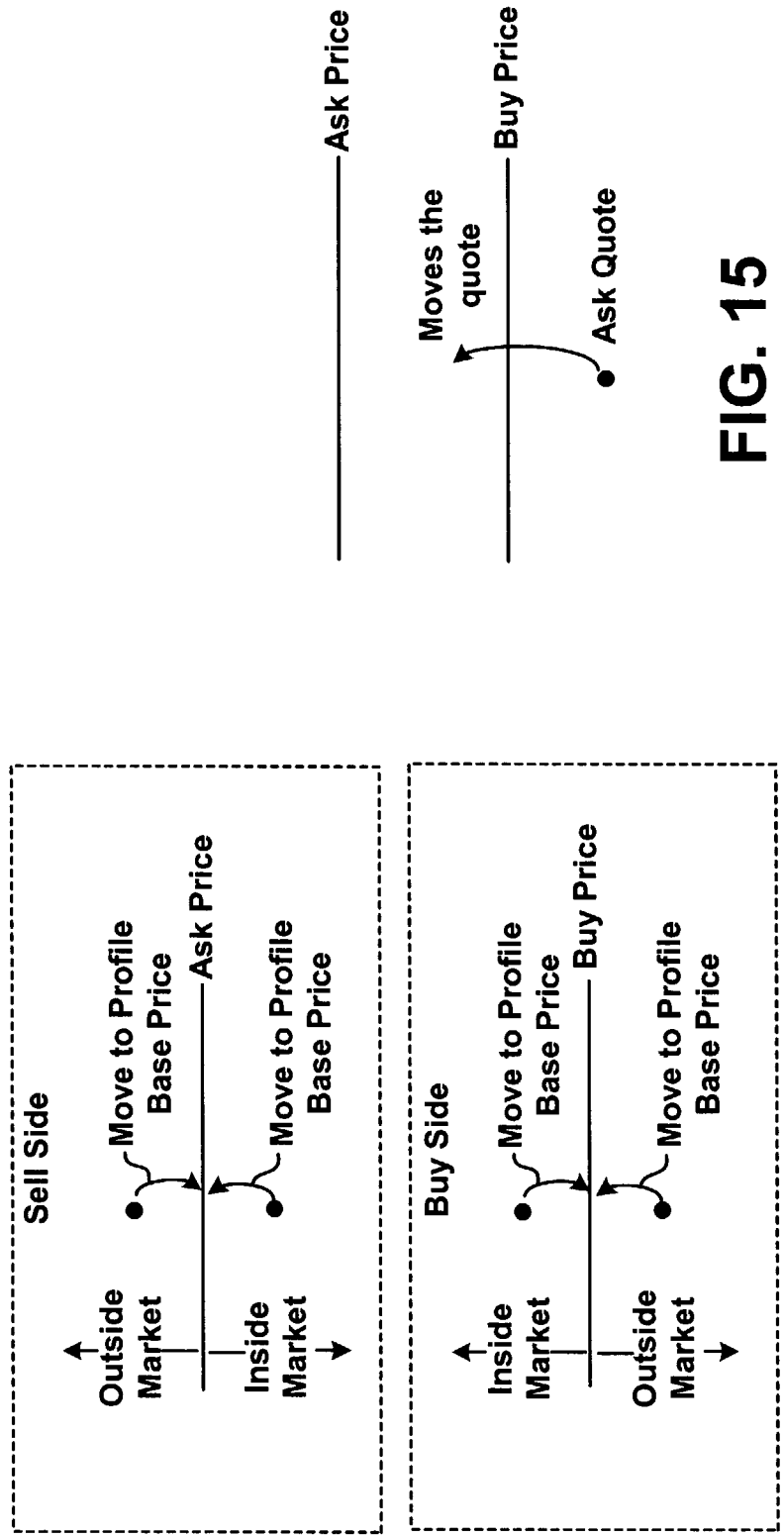
FIG. 14 is a graphical illustration of if quote in, join market and if quote out, join market features.
FIG. 15 is a graphical illustration of an example don't cross-market feature.

FIG. 14 is a graphical illustration of the "If Quote Inside, Join Market" option. When this feature is selected, the system compares the price of the suggested order to price levels that are easily programmed as acceptable to the user. If the price of the suggested order is not at an acceptable price level, then the system preferably changes the price of the order to an acceptable price before it is actually sent to the exchange. The graphical illustration in FIG. 14 provides one example to illustrate this concept. A suggested order is priced below the market ask price (or some other reference price level) on the sell side, however, according to this example, this suggested order price is not at an acceptable price level. Instead of sending the suggested order to the market, the automated trader instead sends an order to the market at a price level which is acceptable, such as the market ask price in this example. Alternatively, the automated trader can send an order at any pre-set price, for example, some pre-set offset value to the market ask price. This can also be applied to the buy side as illustrated in the Figure.

Also shown in FIG. 14 is a graphical illustration of the "If Quote Outside, Join Market" option. This feature is the same as the "If Quote Inside, Join Market" such that when this feature is selected, the system compares the price of the suggested order to price levels that are programmed as acceptable to the user. A difference is that when an order is priced higher (rather than lower) than the market ask price (or some other reference price level) on the sell side, then the system preferably changes the price of the order to an acceptable price before it is actually sent to the exchange. This can also be applied to the buy side as illustrated in the Figure. If desired, the "If Quote Outside, Join Market" and the "If Quote Inside, Join Market" features can be combined into one feature such that if the price of a suggested order is not an acceptable price, the system can automatically change the price of the order to an acceptable price before it is sent to an exchange.

FIG. 15 is a graphical illustration of a "Don't Cross the Market" option which is similar to the above features. For example, if the suggested sell order price has crossed the best buy price, the system can be easily programmed to change the sell order price to an acceptable price before sending the order to the market. In this example, the sell order price is changed to a price level higher than the best buy price, so as not to cross the market.

Sometimes a user might want to designate how much he or she is willing to better the market. The user can do this by entering a value for the "Market Improve Limit" in a field such as shown in FIG. 11. The market improve limit limits the amount by which the traders generated quote improves the best bid price or best ask price in the market. For example, assume that the market improve limit is set to 2 ticks (although any number of ticks or units may be set). Then, if the best bid price is 10 and the best ask price is 20 and a suggested buy order was calculated having a price of 15, a buy order would be sent to the market at a price of 12 and not 15. Thus, the trader in this example is only willing to better the market by 2 ticks. However, if the suggested buy order was calculated having a price of 11, because it falls under the limit, a buy order would be sent to the market at the calculated price of 11. The trader, in this example, is willing to better the market by 1 tick. Of course, the same process can be applied to the buy side. Although only one field is shown for the market improve limit, it is envisioned that the market improve limit can be applied separately to the buy side, the sell side, or it can be applied for both the buy side and the sell side. Preferably, the market improve limit will use the same units as set in the price units field.

The "Quote Move Limit" lets a user specify a limit in units, such as ticks or currency, such that if the suggested order in the scratch pad is greater than the existing quote in the market by more than the limit (in either positive or negative direction), automated trader pulls the existing quote from the market and will not submit the new suggested order. To retrigger automated quoting, the user can click on the "Update Orders" icon.

The "Stale Quote Timeout" lets a user specify the timeout period in seconds such that if the quote in the market has not changed when the timeout limit has been reached the quote is pulled from the market. To retrigger automated quoting, the user can click on the "Update Orders" icon.

Referring to FIG. 3, steps 606 and 608 in FIG. 7 are preferably performed by a strategy processor 212. In a preferred embodiment, the strategy processor 212 can receive information from the profile manager 208, user programmable interface 210, and the market to calculate order parameters such as prices and quantities. Preferably, the strategy processor 212 uses trading limits (e.g., maximum position, quoting limits, allowances, throttling, etc.) to determine whether an order should actually be submitted to the market. In the preferred embodiment, the strategy processor 212 also includes a feature that when enabled prevents orders from crossing the market (e.g., prevents sending an order to market when the suggested buy order is priced greater than the market's best ask price, or prevents sending an order to market when the suggested sell order is priced less than the market's best bid price). When in manual mode, the suggested transactions are passed to the order router 214 when the user selects the "Update Orders" icon. When in automatic mode, the transactions are preferably passed to the order router 214.

In a preferred embodiment, the automated trader also has a cover order processor 222 for calculating and sending cover orders. Alternatively, the cover order processor can be combined with the strategy processor.

At step 610, an order is entered into the market. Referring to FIG. 3, in a preferred embodiment, an order router 214 sends orders into the market and manages the timing of order entry.

At step 612, orders in the market are monitored. Referring to FIG. 3, the strategy processor 212 is monitoring market information and is re-calculating the order parameters (e.g., price and quantity) and thereby calculating new suggested orders. Then, trading limits may be applied to determine if it should replace the working orders in the market with the new suggested orders. If the working orders should be replaced, then the strategy processor 212 indicates to the order router 214 to delete the order and send in a new order (or cancel/replace).

FIG. 16 is an alternative embodiment of the profile window to that shown in FIG. 11. The profile parameter window 1100 allows a user to enter parameters for many tradeable objects of the same type, but having different expiration dates. Thus, a user can put all of the profiles for these tradeable objects into one window. This allows the user to view, edit, create, and/or delete all of the profile parameters for the tradeable objects of the same type. Preferably, automated trader can dynamically pick the appropriate profile for a tradeable object based on the current expiration date of that tradeable object. For example, a user may be trading a tradeable object that has a 60 day expiration date, however, as the date is approached and it becomes a 30 day contract, the automated trader can be programmed dynamically switch to from using the profile of the 60 day expiration date to the profile of the 30 day expiration date.

To distinguish between the tradeable objects having different expiration dates, visual indicators may also be used. In this example, the tradeable objects have been given the names of colors, but alternatively, the user can rename the name of the tradeable objects. According to this example, white, red, green, blue, orange, and copper identify the tradeable objects. Preferably, the automated trader can be programmed to dynamically change strategies based on the expiration day.

FIG. 3, in summary, illustrates a block diagram of an example architecture that is suitable for providing the functionality, described herein. According to this example, modules are integrated to provide the functionality described herein, and include a profile manager 208, user programmable interface 210, strategy processor 212, order router 214, and contract manager 220. In general, a user inputs data into the user programmable user interface 210 and/or the profile manager 208, which is communicated to the strategy processor 212. The profile manager 208 may also communicate data to the user programmable interface 210. The strategy processor 212 calculates order parameters based on the data received from the user and on data received from the market. Results of these calculations can be relayed to the user programmable interface 210. Furthermore, based on these calculations and based on the trading limits, the strategy processor 212 can instruct the order router to send an order (or transaction) to the market. There may be a separate module for sending cover orders to the market when appropriate. Also, a contract manager 220 may provide data about the tradeable objects to the strategy processor and the user programmable interface. As appreciated by those skilled in the art, any programming architecture, whether modular or integrated are a combination of both can be used in conjunction with the present invention. For example, anyone of the example modules described above can be eliminated or combined with another module without departing from the spirit of invention.

Preferred embodiments of the present invention have been described herein. It is to be understood, of course, that changes and modifications may be made in the embodiments without departing from the true scope of the present invention, as defined by the appended claims. The present embodiment preferably includes logic to implement the described methods in software modules as a set of computer executable software instructions. A processor implements the logic. The processor executes software that can be programmed by those of skill in the art to provide the described functionality.

It should be understood that the programs, processes, methods and apparatus described herein are not related or limited to any particular type of computer or network apparatus (hardware or software), unless indicated otherwise. Various types of general purpose or specialized computer apparatus or computing device may be used with or perform operations in accordance with the teachings described herein.

It should further be understood that a hardware embodiment may take a variety of different forms. The hardware may be implemented as an integrated circuit with custom gate arrays or an application specific integrated circuit ("ASIC"). The embodiment may also be implemented with discrete hardware components and circuitry. In particular, it is understood that the logic structures and method steps described in the flow diagrams may be implemented in dedicated hardware such as an ASIC, or as program instructions carried out by a microprocessor or other computing device.

Example Use of Formulas

As previously mentioned, the automated trader allows formula entry into any cell under the "Scratch" column, the "Formulas" column, the Profile Parameter columns, and the Cover order offset column, which are both shown in the automated trader window 300, and also in the cells of the profile window 800. Preferably, each cell accepts many different types of entries such as text, constant numeric values, dates or times, formulas that calculate a value, and graphs. Calculated values may be single numbers or strings, or they can be arrays or tables of values.

Preferably, the formulas can include variables, such as market information found under the "Market" column in the automated trader window 300. For example, if the user wanted to have the current bid price and quantity in his or her formula, then preferably, the user can simply type into the formula the title of the market bid price and bid quantity column. According to this example and the example illustration given in FIG. 4, the user might use variables given by "MktBidPrice" for the current bid price and "MktBidQty" for the current bid quantity in his or her formula. Thus, in a preferred embodiment, the automated trader can calculate relationships among different cells by typing in the row/column coordinates, or address, or name (e.g., "MktBidQty") into the formula.

In one embodiment, formulas entered into the user programmable interface and/or into a profile may be accomplished by a two-way link between the trading interface and a third party software, or may link market data from a trading window into the spreadsheet or other third party software. As known by those skilled in the art, any suitable type of data exchange protocol may be used to embed information from the third party software or to link the dynamic indicator to the third party software. For example, Microsoft OLE 2.0 may be used to perform these functions when using Microsoft Windows applications as the third party software. In a preferred embodiment, Microsoft OLE is utilized to provide a link between cells in the interface and/or profile and a cell from a Microsoft EXCEL spreadsheet. Data exchange protocols in general, and linking and embedding techniques in particular, are well known to those skilled in the art.

Conclusion

The automated trader described herein may be put to advantageous use by providing a user with a simple and flexible trading mechanism to define and implement basic-to-very complex trading programs, allow dynamic entry of program adjustments, automatically monitor market and user data, manage trades, allow efficient configuration of data views, enable order seeding, and more. By using the automated trader, users can quickly and effectively implement program trading with increased functionality and flexibility that can be configured to suit his or her desired trading strategy. Moreover, the automated trader can assist a user in assimilating a large amount of data that is useful in determining his or her trading strategy.

The automated trader may instead be implemented at the communications interface to operate as an intelligent communications interface between one or more third-party software applications and one or more exchanges. This advantageous use of the automated trader allows third-party computer programmers of trading-related software applications to focus their program development on implementing a particular strategy, rather than how to enter orders, how to manage them, and how to place certain limits on the orders. This embodiment allows for simpler third-party applications because the intelligent communication interface takes on more functionality so that the third-party applications do not need to.

It should be understood that the above description of the preferred embodiments, alternative embodiments, and specific examples are given by way of illustration and not limitation. For example, the features described herein could be incorporated into a variety of displays. Many changes and modifications within the scope of the present embodiments may be made without departing from the spirit thereof, and the present invention includes all such changes and modifications.

What is claimed is:

1. A method including:
   receiving, via a user input device of an electronic trading device, a user profile defining a trading strategy for a tradeable object according to user-provided parameters;
   receiving, via a market input device of the electronic trading device, streaming market information for the tradeable object;

automatically continually calculating, via a processor of the electronic trading device, a value for an order price and a value for an order quantity for an order to be sent for the tradeable object, the value for the order price and the value for the order quantity being continually calculated based on the user-provided parameters and the streaming market information according to changes in market conditions as the streaming market data is received;

prior to sending the order, dynamically displaying, via a graphical user interface of the electronic trading device, in a scratch pad area of the graphical user interface, the value for the order price and the value for the order quantity for the order to be sent as the order price and the order quantity are continually calculated;

prior to sending the order, receiving, via the graphical user interface of the electronic trading device in the scratch pad area from a user, a direct entry value, wherein the direct entry value replaces one of the value for the order price and the value for the order quantity for the order to be sent;

prior to sending the order and in response to receiving the direct entry value, stopping continually calculating, via the processor of the electronic trading device, the one of the value for the order price and the value for the order quantity for the order to be sent replaced by the direct entry value;

prior to sending the order and in response to receiving the direct entry value, stopping dynamically displaying, via the graphical user interface of the electronic trading device, in the scratch pad area of the graphical user interface, the one of the value for the order price and the value for the order quantity for the order to be sent replaced by the direct entry value and displaying the direct entry value in the scratch pad area;

prior to sending the order, automatically continually calculating, via the processor of the electronic trading device, the other of the value for the order price and the value for the order quantity for the order to be sent that was not the one replaced by the direct entry value;

receiving, via the electronic trading device, a trigger to send the order to an electronic exchange to trade the tradeable object subsequent to receiving the direct entry value, wherein the order includes the one of the value for the order price and the value for the order quantity replaced by the direct entry value and the other value that was not the one replaced by the direct entry value; and in response to receiving the trigger, sending, via the electronic trading device, the order to the electronic exchange.

2. The method of claim 1, wherein the user-provided parameters include variables.

3. The method of claim 1, wherein the user-provided parameters include values.

4. The method of claim 1, wherein the user-provided parameters include a formula.

5. The method of claim 4, wherein the formula is linked to a software application.

6. The method of claim 1, wherein the user-provided parameters include a bid offset.

7. The method of claim 6, wherein the bid offset includes a value combined with a base profile price for a price for submitting a buy order to the electronic exchange.

8. The method of claim 6, wherein the bid offset includes a negative value.

9. The method of claim 1, wherein the user-provided parameters include an ask offset.

10. The method of claim 9, wherein the ask offset includes a value combined with a base profile price for a price for submitting a sell order to the electronic exchange.

11. The method of claim 9, wherein the ask offset includes a negative value.

12. The method of claim 1, wherein the user-provided parameters include a cover order offset.

13. The method of claim 12, wherein the cover order offset includes a value combined with a base profile price for a price for submitting a cover order to the electronic exchange.

14. The method of claim 12, wherein the cover order offset includes a negative value.

15. The method of claim 1, wherein the user-provided parameters include a reserve offset.

16. The method of claim 15, wherein the reserve offset includes a value combined with a base profile price for a price for submitting a second order when the order is filled.

17. The method of claim 15, wherein the reserve offset includes a negative value.

18. The method of claim 1, wherein the user-provided parameters include a trading limit.

19. The method of claim 18, wherein the trading limit includes a time period for throttling transaction messages sent to the electronic exchange.

20. The method of claim 18, wherein the trading limit includes a maximum position value.

21. The method of claim 20, wherein an open position does not exceed the maximum position value.

22. The method of claim 18, wherein the trading limit includes a bid change allowance.

23. The method of claim 22, wherein the bid change allowance includes a range of price levels relative to the order price of the order outside of which a re-priced buy order is entered.

24. The method of claim 18, wherein the trading limit includes an ask change allowance.

25. The method of claim 24, wherein the ask change allowance includes a range of price levels relative to the order price of the order outside of which a re-priced sell order is entered.

26. The method of claim 1, further including:
receiving, via the electronic trading device, a second trigger to send a second order to the electronic exchange to trade the tradeable object; and
in response to receiving the second trigger, sending, via the electronic trading device, the second order to the electronic exchange, the second order including a re-calculated price.

27. The method of claim 26, wherein the second order includes a cancel/replace order.

28. The method of claim 26, further including sending a delete transaction message to delete the order from the electronic exchange.

29. The method of claim 1, further including sending the order to the electronic exchange automatically.

30. The method of claim 1, wherein the trigger includes a manual trigger.

31. The method of claim 1, further including receiving the trigger via the user input device.

32. The method of claim 1, wherein the trigger is generated by the electronic trading device.

33. The method of claim 1, further including receiving a change to the trading strategy.

34. The method of claim 33, further including changing the trading strategy prior to receiving the trigger.

35. The method of claim 34, wherein changing the trading strategy includes changing at least one of the user-provided parameters.

36. The method of claim 1, further including selecting a second trading strategy to replace the trading strategy, wherein the value for the order price and the value for the order quantity are automatically calculated according to the second trading strategy.

* * * * *